(12) United States Patent
O'Mahony et al.

(10) Patent No.: US 7,230,687 B2
(45) Date of Patent: *Jun. 12, 2007

(54) BLOOD LEAK DETECTOR FOR EXTRACORPOREAL TREATMENT SYSTEM

(75) Inventors: John J. O'Mahony, Barna (IE); Edwin B. Merrick, Stow, MA (US); Sonny Behan, Sugar Hill, GA (US)

(73) Assignee: CHF Solutions Inc., Brooklyn Park, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/217,391

(22) Filed: Sep. 2, 2005

(65) Prior Publication Data

US 2006/0012774 A1 Jan. 19, 2006

Related U.S. Application Data

(63) Continuation of application No. 10/367,875, filed on Feb. 19, 2003, now Pat. No. 6,947,131.

(60) Provisional application No. 60/377,957, filed on May 7, 2002.

(51) Int. Cl.
*G01J 1/42* (2006.01)
*A61B 5/00* (2006.01)
*B01D 35/18* (2006.01)

(52) U.S. Cl. .................. 356/39; 356/410; 600/322; 600/336; 210/96.2; 250/343

(58) Field of Classification Search ........ 356/213–218, 356/432–436, 317–320, 39–41, 410–411; 128/633, 644–645; 250/343, 341; 600/322, 600/336; 210/96 M, 96.2, 118, 188
See application file for complete search history.

(56) References Cited

U.S. PATENT DOCUMENTS 3,832,062 A * 8/1974 Van Den Bosch .......... 356/323

(Continued)

FOREIGN PATENT DOCUMENTS

EP 0 274 178 7/1988

(Continued)

OTHER PUBLICATIONS

Jonathan D. Sackner-Bernstein, MD et al., "How Should Diuretic-Refractory, Volume-Overloaded Heart Failure Patients Be Managed?" The Journal of Invasive Cardiology, vol. 15, No. 10 (Oct. 2003), pp. 585-590.

(Continued)

*Primary Examiner*—Sang H. Nguyen
(74) *Attorney, Agent, or Firm*—Nixon & Vanderhye P.C.

(57) ABSTRACT

A blood leak detector is disclosed having a light source projecting a beam along an optical path, wherein the beam has a wavelength in a range of about 800 to 930 nm; a light detector receiving the beam through an aperture having a diameter in a range of 30 to 60 thousands of an inch; and a housing to receive a tubular liquid passage between the light source and light detector, the housing having a slot transverse to the optical path to receive the tubular liquid passage and the slot has a width narrower than the tubular liquid passage when uncompressed.

40 Claims, 7 Drawing Sheets

U.S. PATENT DOCUMENTS

| | | | | |
|---|---|---|---|---|
| 3,867,925 | A * | 2/1975 | Ersek | 600/528 |
| 4,017,190 | A * | 4/1977 | Fischel | 356/40 |
| 4,085,047 | A * | 4/1978 | Thompson | 210/96.2 |
| 4,227,814 | A * | 10/1980 | Soodak et al. | 356/410 |
| 4,522,494 | A * | 6/1985 | Bonner | 356/39 |
| 4,745,279 | A * | 5/1988 | Karkar et al. | 250/343 |
| 4,784,768 | A | 11/1988 | Mathieu | |
| 4,859,056 | A * | 8/1989 | Prosser et al. | 356/41 |
| 5,206,522 | A * | 4/1993 | Danby et al. | 250/574 |
| 5,247,434 | A | 9/1993 | Peterson et al. | |
| 5,366,630 | A | 11/1994 | Chevallet | |
| 5,670,050 | A | 9/1997 | Brose et al. | |
| 5,674,390 | A | 10/1997 | Matthews et al. | |
| 5,680,111 | A * | 10/1997 | Danby et al. | 340/632 |
| 5,692,505 | A * | 12/1997 | Fouts | 600/336 |
| 5,730,712 | A | 3/1998 | Falkvall et al. | |
| 5,762,805 | A | 6/1998 | Truitt et al. | |
| 5,995,236 | A * | 11/1999 | Roth et al. | 356/445 |
| 6,284,131 | B1 | 9/2001 | Hogard et al. | |
| 6,510,330 | B1 * | 1/2003 | Enejder | 600/322 |
| 6,563,585 | B1 * | 5/2003 | Rao et al. | 356/436 |
| 2001/0016699 | A1 | 8/2001 | Burbank et al. | |
| 2001/0021817 | A1 | 9/2001 | Brugger et al. | |
| 2001/0037079 | A1 | 11/2001 | Burbank et al. | |
| 2001/0041892 | A1 | 11/2001 | Burbank et al. | |
| 2002/0103453 | A1 | 8/2002 | Burbank et al. | |
| 2002/0147423 | A1 | 10/2002 | Burbank et al. | |
| 2003/0009123 | A1 | 1/2003 | Brugger et al. | |
| 2003/0097087 | A1 | 5/2003 | Gura | |

FOREIGN PATENT DOCUMENTS

| | | |
|---|---|---|
| EP | 467805 | 1/1992 |
| EP | 0 990 444 A2 | 4/2000 |
| GB | 1 583 023 | 1/1981 |

OTHER PUBLICATIONS

Brian E. Jaski, MD et al., "Peripherally Inserted Veno-Venous Ultrafiltration for Rapid Treatment of Volume Overloaded Patients", Journal of Cardiac Failure, vol. 9, No. 3, (Jun. 2003), pp. 227-231.

* cited by examiner

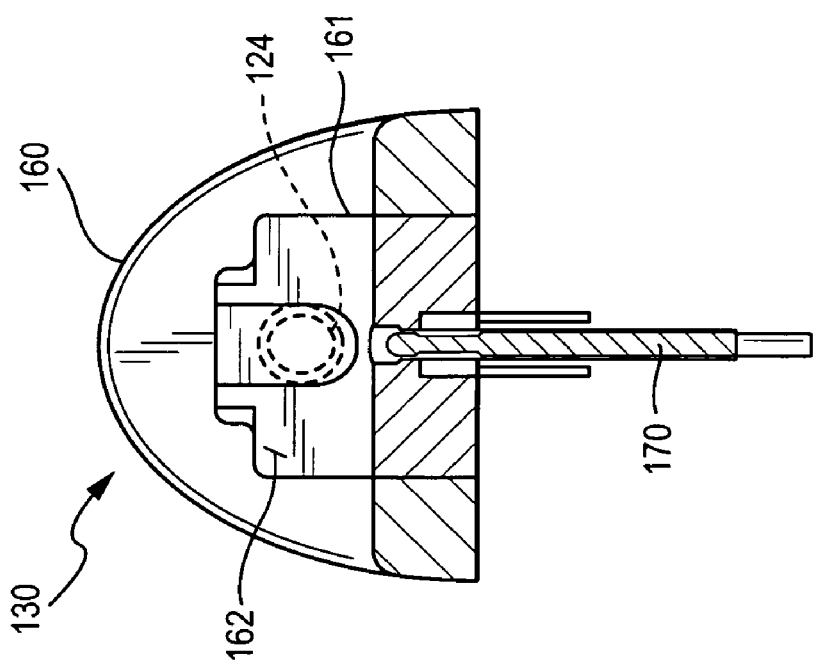
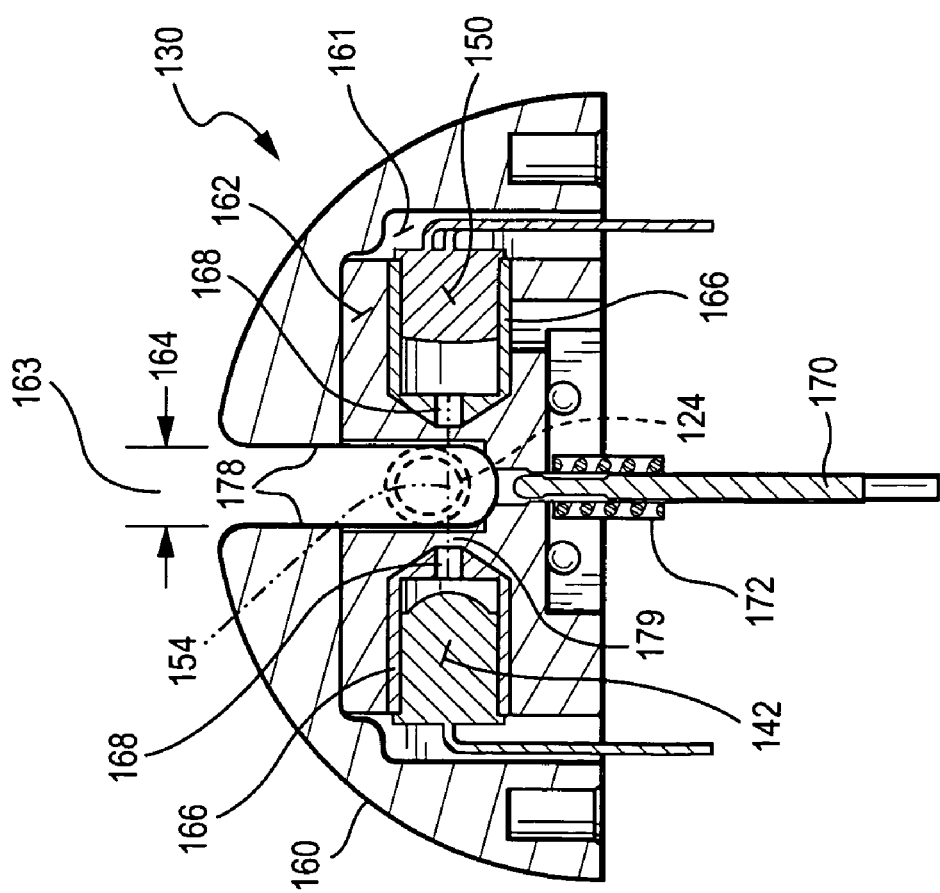

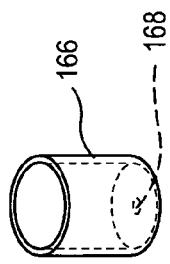
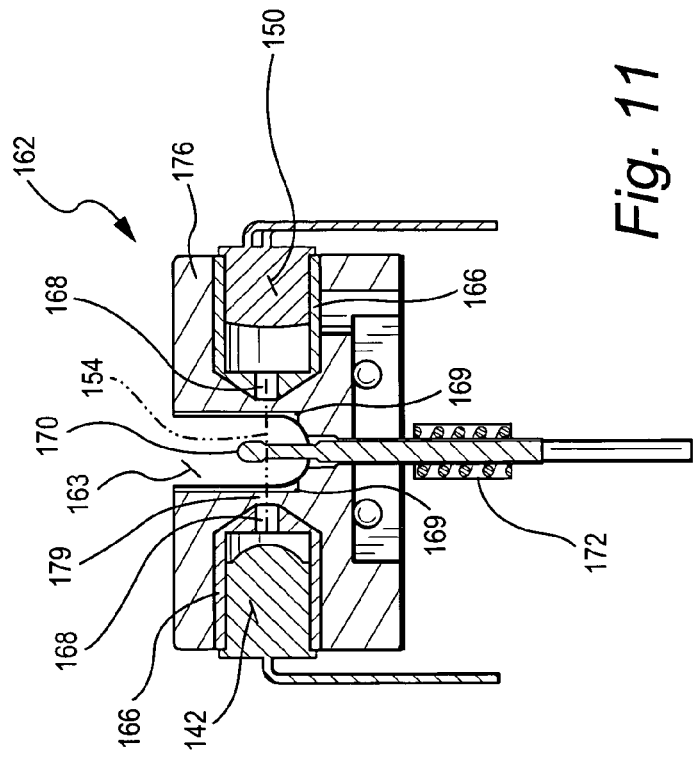
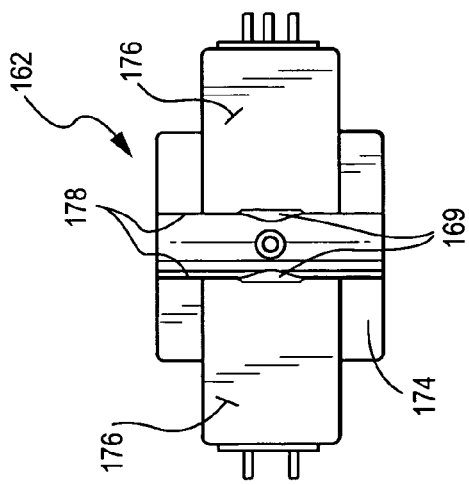
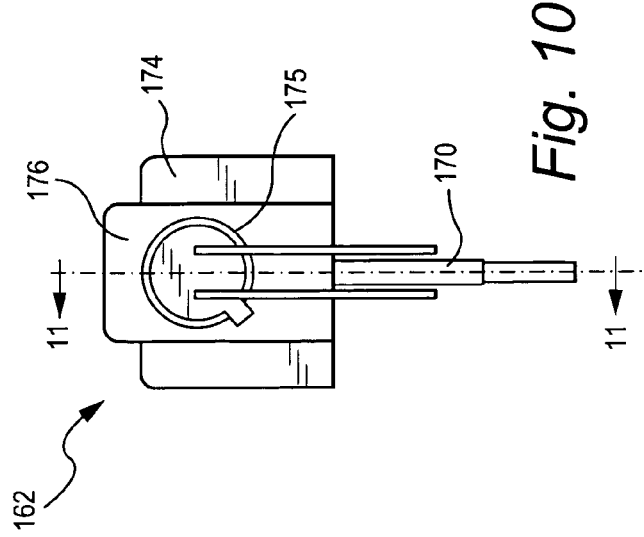

US 7,230,687 B2

BLOOD LEAK DETECTOR FOR EXTRACORPOREAL TREATMENT SYSTEM

RELATED APPLICATIONS

This application is a continuation of U.S. Utility application Ser. No. 10/367,875, filed Feb. 19, 2003 now U.S. Pat. No. 6,947,131, and claims priority under 35 U.S.C. §119(e) to U.S. Provisional Patent Application No. 60/377,957, filed May 7, 2002, the entirety of both applications are incorporated by reference.

BACKGROUND OF THE INVENTION

The present invention relates to the field of extracorporeal blood treatment devices, and in particular to blood ultrafiltration devices.

The present invention provides an improved blood leak detector to sense a rupture or other failure of a blood filter. A blood filter, for example, removes liquid from blood so that concentrated blood can be returned to the circulatory system of a patient. The filter has a blood passage and a filtrate passage that are separated by a filter membrane. The filter membrane allows some liquid to pass, but blocks large solutes and hemoglobin. Hemoglobin, large solutes and a substantial portion of the blood liquid flow through the blood passage of the filter, without passing through the filter membrane. However, if the filter membrane ruptures, hemoglobin and other blood cells and large solutes will flow through the membrane into the liquid filtrate flow. A rupture in the filter membrane can result in loss of desirable hemoglobin and blood cells from the blood being returned to the patient. A rupture in a blood filter should be detected to avoid loss of these blood cells and desirable solutes.

Blood leak detectors are used to detect a rupture in the membrane of a filter by sensing hemoglobin in the filtrate line of the filter. Blood leak detectors rely on the optical sensing of light passing through the blood filtrate tube. A decrease in the amount of light passing through the filtrate tube indicates the presence of hemoglobin in the filtrate and hence a ruptured filter membrane. However, prior blood leak detectors have several shortcomings including: their electronics are prone to drift and require frequent calibration; they are affected by ambient light and require clumsy shrouds to block ambient light from the sensor; they do not detect the absence of a filtrate tube or the absence of a cuvette; they respond differently to oxygenated and unoxygenated hemoglobin; they are difficult to operate and clean, and they tend to be expensive.

SUMMARY OF INVENTION

There is a long felt need for a blood leak detector that satisfies some or all of the following requirements: identifies small and large ruptures of a filter membrane, does not easily drift out of calibration, is equally sensitive to hemoglobin attached and unattached to oxygen molecules, is insensitive to ambient light, detects the absence of a tube or cuvette in the sensor, can be easily cleaned without damaging the sensor or affecting calibration, and is economical. The blood leak detector disclosed here is believed to satisfy these requirements and overcome many of the shortcomings of prior blood leak detectors.

In a first embodiment, the invention is a blood leak detector comprising a light source projecting a beam along an optical path, wherein the beam has a wavelength in a range of about 800 nm to 900 nm; a light detector receiving the beam; and a mount to receive a liquid passage between the light source and light detector.

A second embodiment of the invention is a blood leak detector comprising: a housing having a slot to receive a liquid carrying tube; a light source projecting a beam along an optical path traversing the tube, wherein said light source is mounted in said housing and is adjacent a first side of the slot; a light detector receiving the beam, mounted in said housing and adjacent an second side of the slot; and a mount to receive a liquid carrying tube between the light source and light detector and transverse to the optical path.

In a third embodiment, the invention is a blood leak detector comprising: a light source projecting a beam along an optical path; a light detector receiving the beam; a mount to receive a liquid passage between the light source and light detector and transverse with the optical path; and a retractable vane having an extended position blocking the beam and in front of the light detector.

In a fourth embodiment, the invention is a blood leak detector comprising: a housing having a slot to receive a liquid carrying tube with a recess on each side of the slot greater than the width of the tube; a light source projecting a beam along an optical path transverse to the tube, wherein said light source is mounted in said housing and is adjacent a first side of the slot; a light detector receiving the beam, mounted in said housing and adjacent an second side of the slot; and a mount to receive the liquid tube between the light source and light detector and aligned with the optical path.

BRIEF DESCRIPTION OF THE DRAWINGS

FIG. 7 is a cross-sectional view of the blood leak detector taken along line 7-7 in FIG. 6;

FIG. 8 is a cross-sectional view of the blood leak detector taken along line 8-8 in FIG. 5;

FIG. 9 is a top view of a light source and sensor module for the blood leak detector;

FIG. 10 is a side view of the light source and sensor module shown in FIG. 9;

FIG. 11 is a cross-sectional view of the light source and sensor module taken along line 11-11 in FIG. 10; and FIG. 12 is an isometric view of a cylinder housing for the photodiode and light emitting diode (LED) that contains an aperture for a light path between the photodiode and LED.

DETAILED DESCRIPTION OF THE INVENTION

Figure 1:
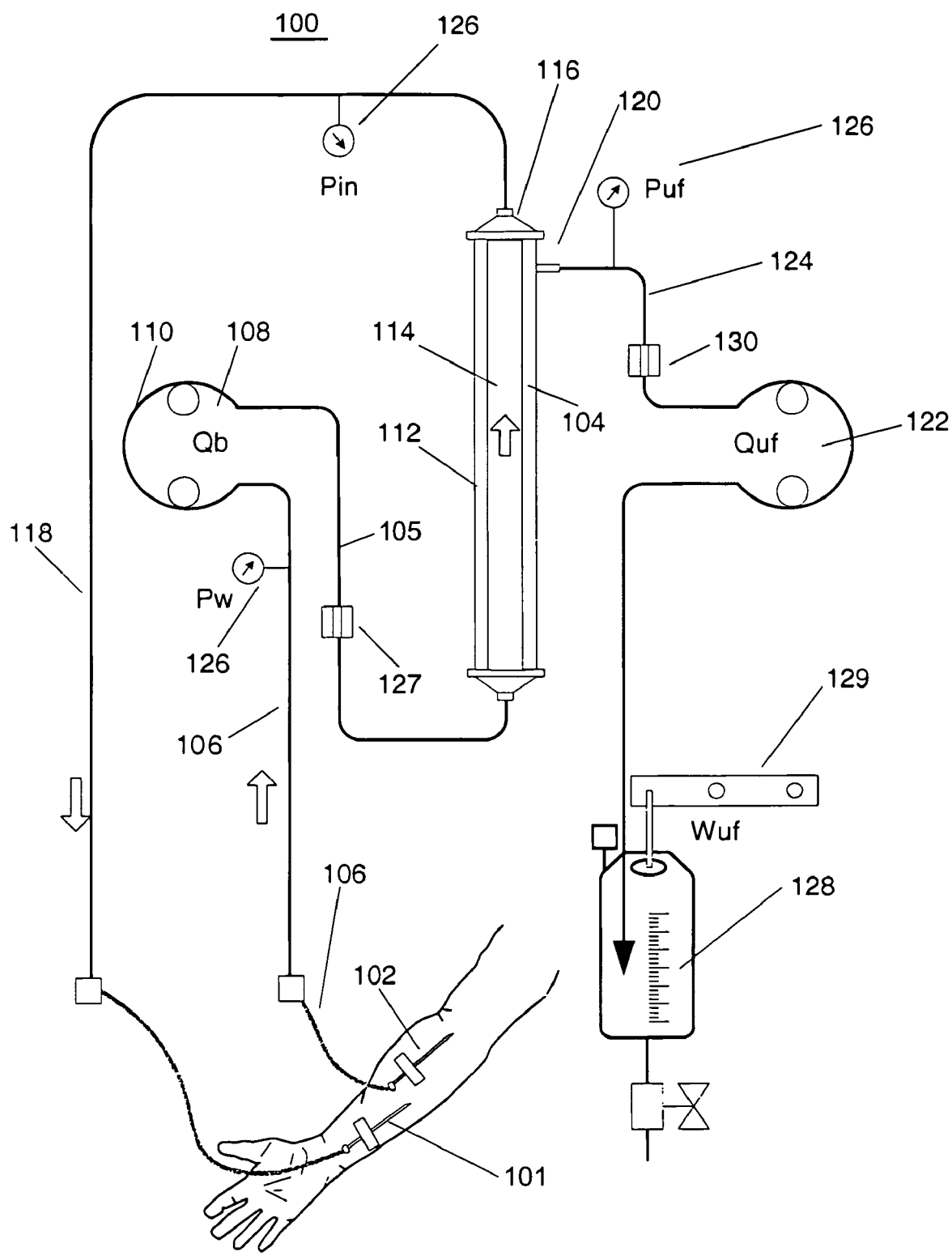
FIG. 1 is a schematic diagram of an ultrafiltration extracorporeal circuit.

FIG. 1 depicts the major components of a blood ultrafiltration system 100 that extracts blood from a vein or artery in a patient 102, removes liquid from the blood in a filter 104, and returns condensed (also referred to as concentrated) blood to the same or other vein or artery of the patient. Condensed blood is blood from which liquids have been removed by ultrafiltration. The hematocrit of condensed blood is generally higher than of the blood before condensation. The ultrafiltration system benefits patients suffering from liquid overload, such as often occurs in patients having a chronic heart failure (CHF) condition. By filtering excessive liquid from the blood, these patients are relieved of the discomfort of liquid build up in their lungs, extremities and other portions of their body.

To withdraw blood, a withdrawal tube 106 is connected to a withdrawal cannula 102 inserted into a vein of the patient. The tube 106 leads the withdrawn blood to a blood pump 108 which acts on a tube loop 110 to move blood through the blood tubing. The rotational speed of the blood pump controls the withdrawal flow rate (Qb) of the blood through the withdrawal tube 106. From the pump 108, blood flows through the blood tube 105 to the filter 104.

The filter 104 may be a filtration column 112 housing a large area filter membrane 114 that separates a blood passage(s) through the filter from a filtrate passage of the filter. The membrane 114 is porous to liquid and may pass small solutes. The size of solutes that pass through the membrane depends on the porosity of the membrane. A first surface of the filter membrane 114 forms a portion of the blood passage wall through the filter column 112, and is exposed to blood flowing through the filter. In the filter, much of the blood flows through the blood passage, over (but not through) the first surface of the membrane, and out the blood output 116 of the filtration column. The blood leaving the blood output 116 flows from the filter, through the infusion tube 118 and is returned to the patient via an infusion cannula inserted into a peripheral vein of the patient 101.

A portion of the blood flowing through the filter 104 passes through the filter membrane 114, and flows to a filtrate outlet 120 of the filter. A filtration pump 122 withdraws ultrafiltrate from the filter and through filtrate tube 124. Due to suction applied to the filtrate tube, the filtration pump controls the filtrate flow rate (Quf) from the filter. Pressure sensors 126 in the withdrawal tube 106 (see Pw), infusion tube 118 (Pin) and filtrate tube 124 (Puf) monitor the pressure of the blood and filtrate flowing through the system 100. A bubble detector 127 monitors the blood tube 105 for air bubbles.

The ultrafiltrate flows from the filter 104, through filtrate tube 124, and into a filtrate collection container 128, which is typically a collection bag with graduations to indicate the volume of ultrafiltrate removed and in the bag. A weight scale 129 monitors the weight (Wuf) of collection container 128.

A blood leak detector 130 monitors the filtrate tube 124 for the presence of blood hemoglobin in the filtrate. Blood hemoglobin in the filtrate indicates a rupture in the filter membrane. The detector 130 optically monitors the filtrate for the presence of hemoglobin by sensing the absorption of a light beam passing through the filtrate tube 124. Hemoglobins are large blood molecules that are too large to pass through the membrane of a properly functioning filter. If hemoglobin molecules do pass through the membrane, the filter membrane has likely ruptured. The detector 130 transmits a light beam of a particular wavelength through the filtrate line and senses the amount of light absorbed by the filtrate. The absorption of light in the infrared spectrum between 800 and 900 nm is strongly influenced by the presence of hemoglobin in the filtrate.

Figure 2:
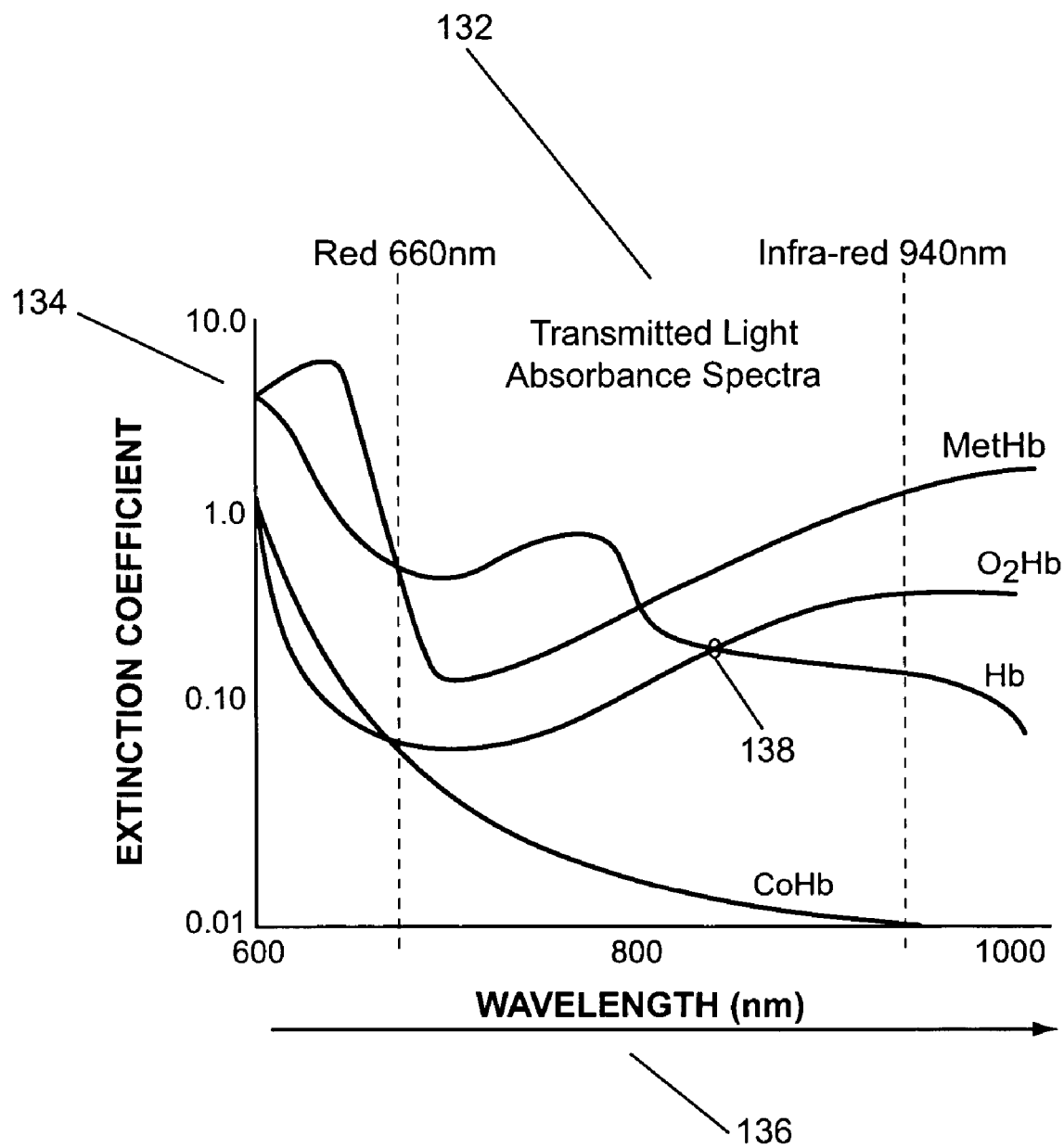
FIG. 2 is a chart of light extinction curves (Zijlstra) for various types of blood hemoglobin.

FIG. 2 is a chart 132 showing the light absorption 134 (in terms of molecular extinction coefficients) of different types of hemoglobin at various wavelengths 136 between 600 to 1000 nanometers (nm). The molecular extinction coefficient 134 is a property of each hemoglobin type at each wavelength. The different types of hemoglobin that are charted include hemoglobin without an oxygen molecule (also referred to as de-oxy hemoglobin) and hemoglobin combined with an oxygen molecule (oxy-hemoglobin), which are the two most common forms of hemoglobin. De-oxy hemoglobin (Hb) and oxy-hemoglobin ($O_2Hb$) in the filtrate are sensed by the blood leak detector. The other types of hemoglobin charted in FIG. 2 are extraordinary and are carboxy hemoglobin (CoHb) (which generally occurs in the blood of fire victims), and cyan-hemoglobin and methhemoglobin (MetHb) (which generally occur in the blood of poison victims). For purposes of a blood leak detector for an ultrafiltration system, the optical properties of these extraordinary types of hemoglobin, i.e., carboxy-, cyan- and methhemoglobins, are being ignored.

The two most common hemoglobins (oxy and de-oxy) have identical or near light absorption characteristics, known as extinction coefficients, at 820 nm, as is shown in the chart 132 at point 138. The light absorption of oxyhemoglobin ($O_2Hb$) and de-oxy hemoglobin (Hb) is substantially the same for wavelengths from about 800 nm to 930 nm as shown in FIG. 2, and from about 250 nm to 600 nm (not shown). The blood leak detector senses light at or near 820 nm, e.g. between 800 to 930 nm, to be generally equally responsive to oxy- and de-oxy hemoglobins flowing in the filtrate tube.

The blood leak detector exploits the fact that the extinction coefficients of oxy and de-oxy hemoglobin are substantially equal in the range of wavelengths from about 800 nm to 930 nm. By emitting a light beam in this range, the blood leak detector is relatively insensitive to blood oxygenation because the light adsorption characteristics are substantially the same for oxy and de-oxy hemoglobin. Commercially available solid state light sources and detectors that are responsive at 820 nm wavelengths may be selected for use in the blood leak detector 130.

The blood leak detector 130 utilizes a light source, e.g., light emitting diode (LED), and a matched light detector, e.g., photodiode, that have narrow spectral emission and detectivity curves. The spectral optical peak of these devices is preferably 800 nm to 930 nm (nano-meters) in the infrared spectrum. These wavelengths of light are equally absorbed by oxy- and de-oxy hemoglobin. Due to its narrow spectral zone and housing, the blood leak detector 130 is not substantially affected by ambient light. The blood leak detector may also include a modulated drive for the LED (light emitting diode) and a synchronous demodulator that are arranged to further reduce the responsiveness of the detector to ambient light interference.

The blood leak detector 130 includes a defined optical path 154 (see e.g., FIGS. 7 and 11) of a fixed dimension, e.g., length, that passes through the filtrate tube 124. This optical path 154 is within the detector and extends from a light source to a light sensor. In a defined optical path of fixed dimensions, the optical transmission of a non-scattering absorber will obey the Beer-Lambert Law. This law can be stated for hemoglobin absorption as a relationship between Beer's Law Transmission and blood concentration, as follows:

$$T_C = Io \cdot 10^{-k \cdot \frac{C}{100} \cdot d}$$

Where $T_C$ is the optical transmission of the filtrate containing hemoglobin; C is the concentration of blood in the filtrate tube (expressed in percentage points between 1 and 100); k is the modified molecular extinction coefficient of the hemoglobin for both de-oxy and oxy-hemoglobin at a wavelength of 820 nm); d is the thickness of the blood sample in the optical path for example, d is 3.0 mm (for a filtrate tube having an internal diameter of 3.2 mm and an external diameter of 4.7 mm); and Io is the initial voltage output of the light sensor 150, after having passed through a transimpedance amplifier and demodulator circuit, when no blood is present in the filtrate tube.

Experimental measurements are usually made in terms of transmittance (T), which is defined as:

$$T=I/Io$$

Where I is the intensity light after it passes through the sample and is received by a light detector, and Io is the initial light intensity of the light with no sample present. Percent Transmittance is defined as:

$$\% \ T=T*100$$

Figure 3:
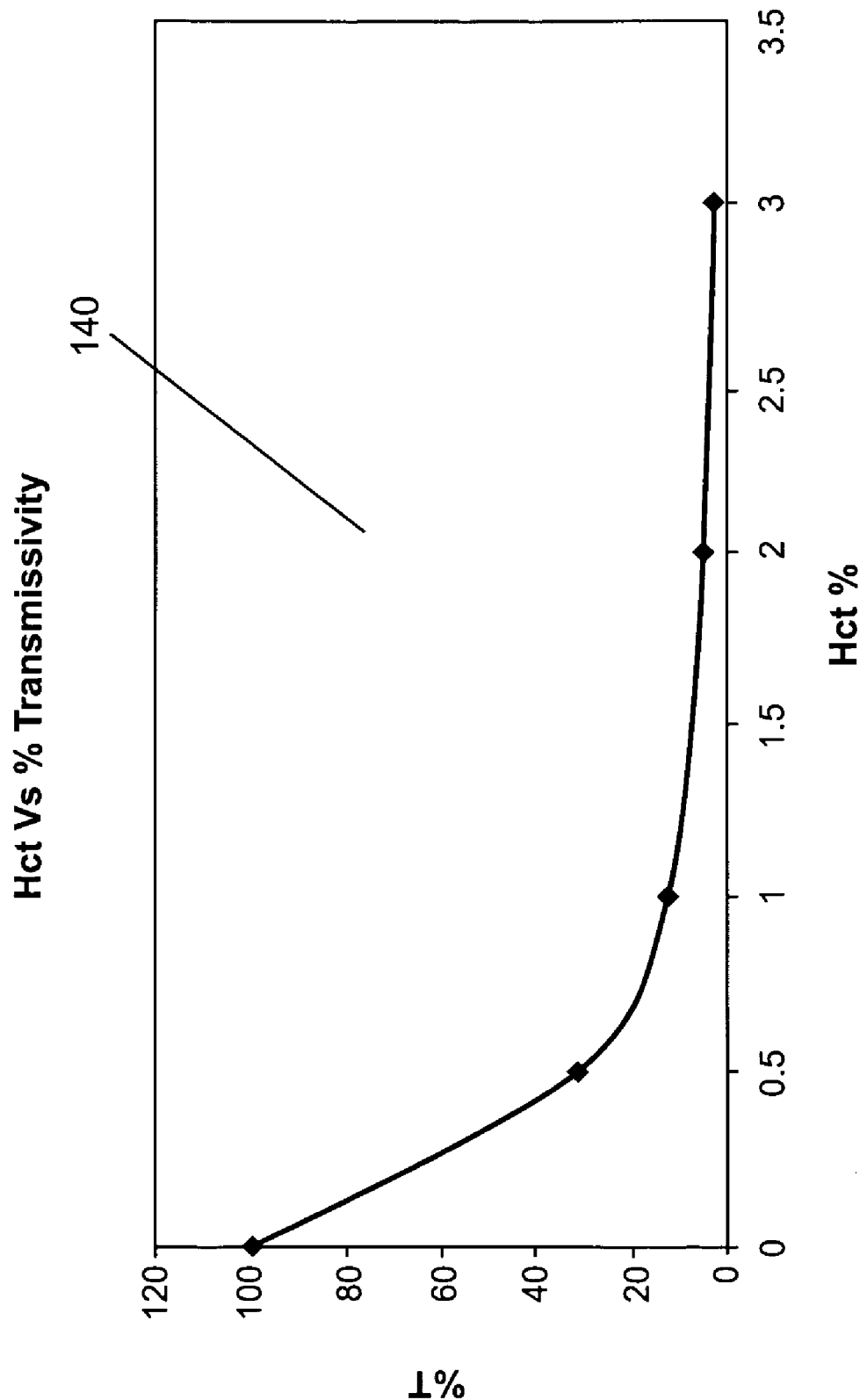
FIG. 3 is a graph of light transmission for various concentrations of blood in filtrate.

FIG. 3 is a chart 140 of the relationship between the percent light transmission (% T) and hemoglobin concentration from a blood leak detector. Hematocrit (Hct) is a term used to describe the concentration of red blood cells (RBC) or hemoglobin in blood or in this case ultrafiltrate. Hematocrit (Hct) is the percent of whole blood that is comprised of red blood cells (RBC). The hematocrit is a relative measure of RBC volume. As the blood concentration (Hct) in the filtrate increases, the optical transmission (% T) decreases. Due to the non-linearity of Beer's Law, the sensitivity to hemoglobin is high at low concentrations, as shown for (Hct) concentration levels from 0 to 2.

Due to high sensitivity, the blood leak detector 130 is highly responsive to the presence of even small amounts of hemoglobin in the filtrate line. A sensor 130 may be calibrated and normalized to a condition in which there is no tube or interference present in the light path 154. During calibration, a filtrate carrying tube was inserted into the light path, where the tube was sequentially filled with liquids having Hct levels of 0.5%, 1%, 2% and 3% yielding a % T of 31.2%, 12.5%, 5.1% and 2.3% respectively. Light sensor measurements were made at each of these Hct levels, and these measurements were stored in a pump controller to serve as reference points for future measurements of light passing through a filtrate tube during a blood treatment process. These measurement values may be applied for all blood leak detectors having similar light source, detector and supporting electronics. A sensor of this design can be easily used to detect concentration of less than 0.5% Hct in ultrafiltrate.

To calibrate an individual blood leak detector, a few optical reference conditions are determined and recorded. To determine these conditions, the optical path (which normally extends through the filtrate tube, but for which the tube is removed for calibration) is occluded with an opaque material, such as a vane 170 (FIG. 7) inserted to block light from reaching the sensor of the detector. Offsets of the electronics are recorded as a zero condition ($I_0$ at 0% transmittance) measured by the detector when its optical path is occluded. The vane 170 is then removed and the output of the sensor is recorded ($I_{100}$ at 100% transmittance) without any interference in the light path. The blood leak detector sensor is now calibrated for a normalized output with these two sets of readings.

An optical filter, such as a neutral density filter, is then introduced into the optical path of the blood leak detector while the filtrate tube is still not inserted into the detector. When the neutral density filter is in the optical path, the light sensor output value is stored as ($I_{ND}$). The neutral density filter is selected to have similar density of the ultrafiltrate carrying tube with a blood (hemoglobin) hematocrit level that is intended to be the threshold level ($I_{ND}$) to be detected. For example, if the threshold concentration level in the filtrate tube to be detected is a 2% Hct of blood in the ultrafiltrate, then the neutral density filter is selected to have a similar optical transmission at 820 nm to filtrate having a concentration of 2% blood. During calibration, the blood leak detector temperature may also be recorded.

In use, the transmission (% T) of the ultrafiltrate is calculated as:

$$\% \ T=100(I_u-I_0)/(I_{100}-I_0)$$

Where $I_0$ is the first reference condition; $I_u$ is the voltage output of the detector 130 (FIG. 1), after amplification, demodulation and filtering, at the use condition (where the use condition is filtrate flowing through the filtrate tube), and $I_{100}$ is the second reference condition.

The photodiode light detector 150 may be subject to sensitivity changes due to temperature. This will have the effect of falsely increasing or decreasing the blood leak detector reading by as much as 8% of the % transmittance reading due to a 15 degree Celsius difference in temperature. It was found that the sensitivity of the photodiode to temperature was linear and consistent between sensors when the % T was measured over the temperature range of 10 to 50 deg Celsius. Thus by calibrating each blood leak detector sensor at a known temperature, the effect of temperature on the photodiode sensitivity can be nullified by compensating for the temperature effect with a correction factor. The reference temperature for the blood leak detector sensors may be selected as 25 degree Celsius. The temperature correction factor (CF) may be treated as a constant for all blood leak detector sensors and can be accounted for by:

$$CF=1+TC \times (T_{b2}-T_{b1})$$

$$\% \ T_u = CF \times \% \ T$$

where % Tu is the corrected measured transmittance; CF is the temperature correction factor and is combined temperature coefficient of the light emitting diode (LED) and photodiode; TC is the magnitude of the temperature coefficient; $T_{b1}$ is the calibration blood leak detector temperature measured using a thermistor housed in the sensor; $T_{b2}$ is the temperature at the use condition; and % $T_u$ is the updated % T accounting for the current temperature of the blood leak detector. The CF correction factor is applied when the blood leak detector transmittance is measured. The CF correction factor normalizes each % transmittance reading taken to a temperature of 25 deg. C.

The transmittance of the neutral density filter at the time of calibration is stored in non-volatile memory of a controller for the blood pump or blood circuit. If the corrected measured transmittance (% $T_u$) is less than the desired ultrafiltrate blood threshold (% $T_{uf}$), then a blood leak detection alarm will be annunciated by the system electronics.

Figure 4:
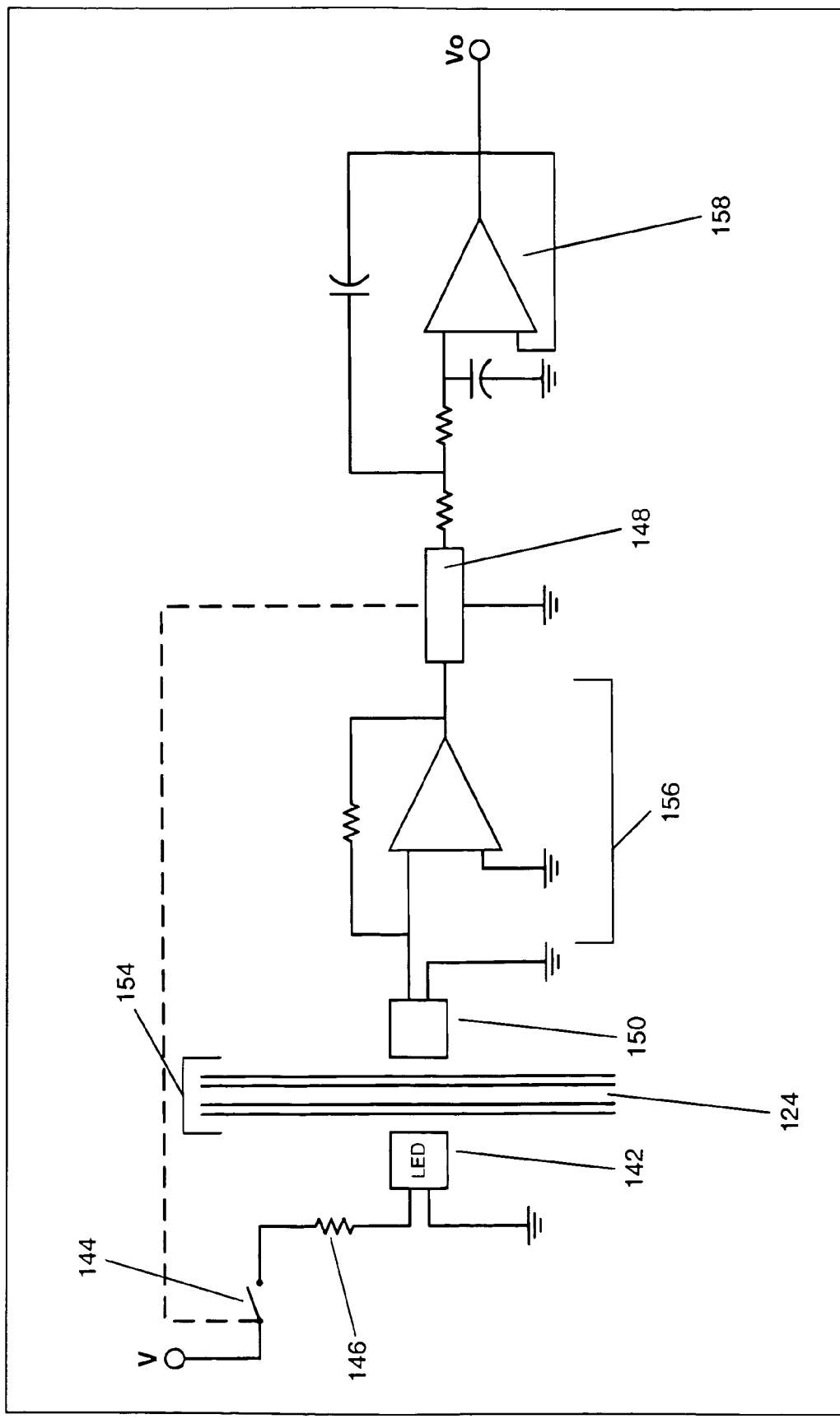
FIG. 4 is an electronics schematic diagram of driver circuits for a light emitter and sensor in a blood detector.
Figure 6:
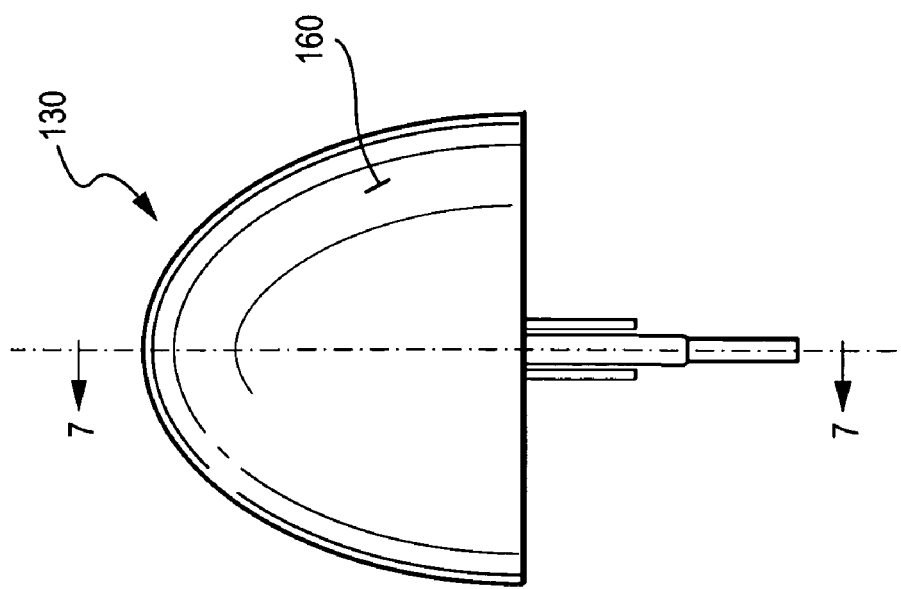
FIG. 6 is a side view of the blood leak detector shown in FIG. 5.

FIG. 4 is a schematic diagram of an exemplary drive circuit 141 for the LED 142 and amplification and demodulation circuitry for the signal of the optical sensor 150 in the blood leak detector. The driving circuit 141 for the LED includes a switch 144 in series with a resistor 146. The switch 144 may be operated by a square wave or other duty cycle, at a frequency in the range of 100 to 20,000 Hz. The current supplied to the LED is a chopped current of a particular phase and frequency. The demodulator 148 for the light sensor, e.g., photodiode, 150 is operated at the same frequency and phase as the LED drive. Because ambient light will not have the same modulation frequency, the effect of ambient light is eliminated in the demodulation process.

The filtrate tube 124 containing ultrafiltrate with potential blood contamination is in the optical path 154 between the LED 142 and the sensor 150. Light from the LED passes through the tube 124 and impinges on the photodiode sensor 150. The photodiode 150 produces a current signal in response to the light, and the signal is amplified by a trans-impedance amplifier 156. The gain of the trans-impedance amplifier 156 produces a usable signal that is demodulated and applied to an electronic filter 158. The filter 158 removes the synchronous drive frequency and its harmonics, which is the common frequency applied to both the switch 144 and demodulator 148. The combination of the frequency of the drive applied to the LED and the demodulator and filter effectively filters out, from the sensor signal, effects of ambient light and other potential interfering signals. The output ($V_o$) of the filter is a voltage proportional to the intensity of the light energy originating at the LED 142, traversing the path 154 through the ultrafiltrate carrying tube, and impinging on the photodiode 150. The LED may be selected to emit a particular wavelength, such as between 800 to 930 nm, and 820 nm in particular. Similarly, the photodiode may be selected to be most responsive to the wavelength(s) emitted by the LED resulting in the photodiode being less sensitive to other light spectra.

The chopped current drive frequency should be selected to be other than line frequency, e.g., 50/60 cycles per second and different from line frequency harmonics. The demodulator 148 must be synchronized at the same frequency and phase as the drive of the LED. By employing a synchronous demodulation scheme that responds to the frequency and phase of the driver of the LED, the demodulator is insensitive to ambient light. The operation of the demodulator is as follows. Pairs of signal strength readings are made from the photodiode light detector a first when the LED is ON and then a second when the LED is OFF. A difference is determined from a comparison of the light detector signal strengths with the LED is ON and with the with the LED OFF. The signal strength difference is relatively free of the influence of ambient light that may pass through the slot in the housing and reach the photodiode light detector. The frequency at which the pair of signal strengths readings are taken must be significantly higher than the frequency of the variation in ambient light such that the level of ambient light is generally the same while each pair of signal strength measurements are taken. For instance if the intensity at 820 nm of ambient light is "A" and intensity of the LED at the same wavelength is "I", then the reading of the photodiode when the LED is OFF=A and the reading when the LED is ON=I+A. When the synchronous readings are subtracted from each other ON−OFF=I+A−A=$I_{diff}$.

The voltage output signal (Vo) from the blood leak detector filter 158 may be interfaced through an analog-to-digital (A/D) converter to a microprocessor which has the capability to store numbers and perform basic arithmetic operations. The A/D converter and microprocessor may be in the controller for the pumps of the blood ultrafiltration system 100. The microprocessor may stop the ultrafiltrate pump 122 (FIG. 1), if the photodetector output signals ($V_o$) is less than a predefined threshold level. A below threshold output signal indicates that hemoglobin is in the filtrate and that the filter membrane has ruptured.

Figure 5:
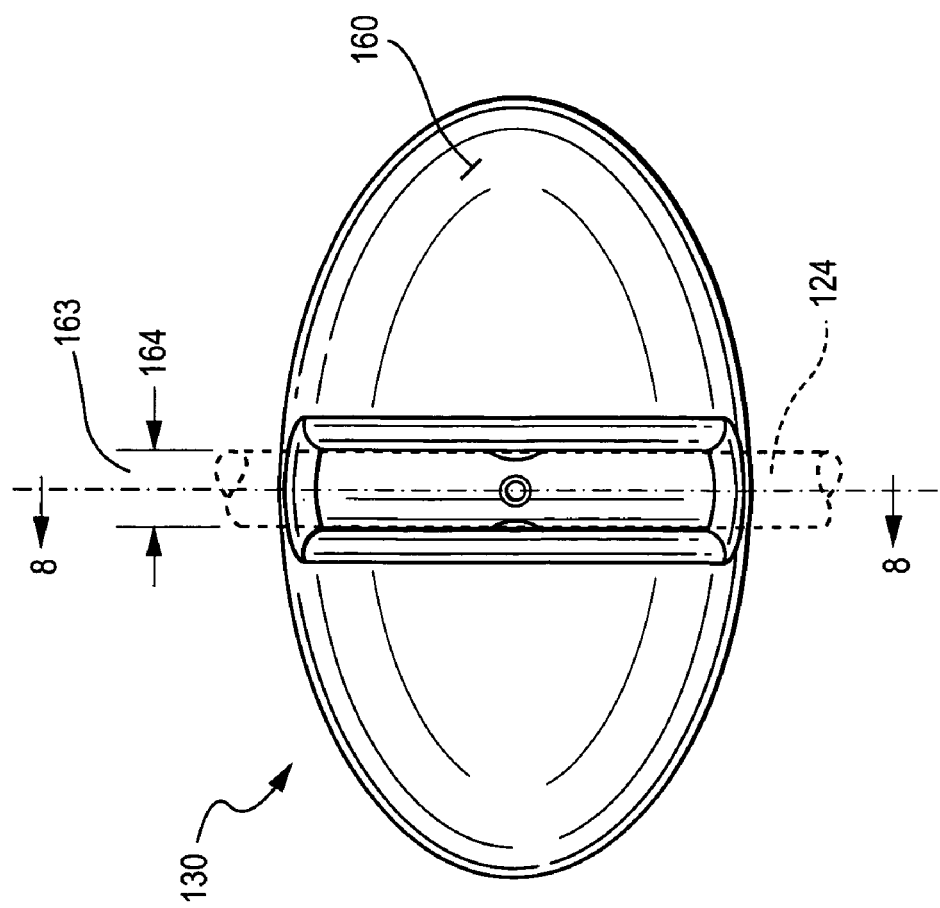
FIG. 5 is a top view of a blood leak detector.

Extreme ambient light may overdrive the trans-impedance amplifier 156. However, extreme ambient light is blocked from the photodiode 150 by the housing 160 (FIG. 5) and the black polymer cylinders 166 (FIGS. 7 and 12) for the blood leak detector. The relatively high sides of a slot 166 through the housing and the narrow aperture of the bores 168 for the light path 154 shield the photodiode 150 from direct ambient light. To minimize reflecting or conducting ambient light toward the photodiode, the surfaces of the optical device housing are opaque and non-reflective at the operative wavelength of the LED, such as 820 nm. This is achieved with the use of a black ABS cylinders 166 for housing the photodiode and LED, where the cylinder has an aperture (bore 168) of a diameter of 30 to 60 thousands of an inch (0.030 inch to 0.060 inch). The bore for the photodiode minimizes stray beams of light close to 820 nm from penetrating through to the photodetector.

FIGS. 5 to 8 show top, side and cross-sectional views of the blood leak detector 130. The substantially hemi-elliptical outer surface of the housing body 160 of the detector is formed of a material, e.g. opaque plastic, that blocks ambient light, particularly at the wavelengths of the light emitting diode (LED) 142, e.g., 820 nm. The housing body 160 has a smooth surface that can be easily wiped clean. The housing body has a cavity 161 open to a bottom surface of the body 160. The cavity 161 receives a light emitter and sensor module 162 (see FIGS. 9 to 11) that includes the light emitting diode (LED) 142 and photodiode 150. The module 162 may be sealed within the cavity 161 of the housing body during assembly of the detector. Sealing the module protects the module from wear and tear. The housing 160 also shields the module 162 from dirt and fluids.

A gap or slot 163 through the center of the housing body 160 extends between the LED and photodiode. The gap provides a recess to receive an ultrafiltrate tube 124. The width 164 of the gap 163 is smaller than the width of the ultrafiltrate tube 124 in order to securely hold the tube in the detector and to assist in maintaining a uniform length light path 154 (FIG. 7). The gap may have rounded corners at its bottom to seat the ultrafiltrate tube and facilitate the cleaning and removal of debris and fluid from the slot.

The light path 154 extends from the LED 142, through the gap 163 and ultrafiltrate tube 124, and to the photodiode 150. The filtrate tube 124 used to transport the ultrafiltrate should be transparent to the selected light spectra or it will attenuate the light signal. The gap 163 squeezes the tubing 124 to reduce the tubing diameter between 50% and 90% of the uncompressed tube diameter. By squeezing the tubing, the tube 124 is made flat against the slot sidewalls and at the interface to the light window where the apertures reside, which further minimizes false attenuation due to reflection by the tubing surface. If the tube remains round, the curved surfaces of the tube in the light path 154 could cause reflection that could severely attenuate the normalized signal (Vo) and result in false detections of the presence of blood in ultrafiltrate.

The LED 142 and photodiode 150 are recessed in the housing of the module 162 and set back from the gap 163 in order to protect the debris sensitive optical ends of the bores 168, for the LED and photodiode. Within the module 162, the LED and photodiode are each mounted in respective cylinders 166 (FIG. 12) that may be formed of black polymer such as ABS or Delrin. The ends of the cylinders 166 have bores 168 (narrow light apertures) that are aligned with the optical ends of the LED and photodiode and the light path 154.

Within the module 162, the LED and photodiode are mounted in opaque cylinders 166. These cylinders 166 have bores 168 e.g. optical apertures, aligned with the axis of the cylinders and the optical path 154. The bores 168 in the opaque cylinders 166 may be open or filled by a cylinder plug or window formed of polycarbonate or polyvinyl chloride transparent to the light from the LED. The narrow diameter bores 168 confine the light path 154 to rays that pass through ultrafiltrate carrying tube 124. The bores provide a narrowly-defined optical path that projects directly through the ultrafiltrate tube 124 and avoids the need for a cuvette. The bores of the cylinders 166 and the body of the module 162 are transparent to the infrared spectrum and thus act as a window for the light path. Further, the transparent module 162 excludes debris and other contaminates from entering the light apertures of the LED, detector and cylinders 166. In addition, the light path 154 is shielded by the narrow bores and the relatively-high sidewalls of the light path gap 163 through the opaque body 160 and the polymer cylinders 166.

Shallow recesses 169 (FIG. 11) in the gap sidewalls 178 of the housing body 162 are provided to set back the LED and photodiode cylinder housings 166 from the filtrate tube 124 and thereby prevent abrasion of the optical face of the bores 168 and avoid a build up of dirt on the transparent bores. Scratches and dirt on the front faces of the bores 168 could falsely attenuate the transmittance of the ultrafiltrate tube and lead to the incorrect declaration of a blood leak alarm. The recesses 169 should be wider than the than the diameters of aperture bores of the cylinders 166 and the depth of the recesses may be between 0.010 to 0.060 inch.

A spring-loaded vane 170 (FIG. 7), opaque at 820 nm, provides a fail-safe mechanism to indicate a high blood concentration if the tube should be displaced from the optical path. The spring-loaded shutter vane 170 blocks light from the LED, when the filtrate tube 124 is out of the optical path 154. When the tube 124 is not present, a spring, 172, extends the vane 170 to block the light path 154 and obstructs the beam of light from the LED 142 to the detector 150. The spring 172 allows the vane 170 to retract when the filtrate tube 124 is inserted into the optical path. Alternatively, the vane 170 may be activated by a gravity operated lever that obstructs the optical path 154 when the ultrafiltrate tube is not present in the gap.

FIGS. 9 to 12 show the inner LED and photodiode module 162 which may include a housing 174 that is transparent to light spectra between 800 and 930 nm of the blood leak detector. The module housing 174 has side holes 175 to receive the opaque cylinders 166 which support the LED and photodiode. The gap 163 for the filtrate tube extends between housing blocks 176 of the module. The housing blocks 176 are transparent to ambient light and protect the opaque cylinders 166 from occlusion by dirt or debris. The sidewalls 178 of the housing blocks 176 contain the recesses 169 (FIG. 9) which separate the window covering the cylinders 166 from the gap 163. The detector 130 may be an integral assembled unit that can be mounted on a blood pump and controller. A portion 179 of the sidewalls 178 are aligned with the bores of the cylinders 166 and serve as windows for the light path 154. These window portions 179 are transparent to the light from the light source 142.

The blood leak detector 130 uses selected optical components, stable signal processing electronics, is equally sensitive to oxy- and de-oxy hemoglobin, employs a housing 160 which contains a transparent housing 162 in which are mounted two opaque cylinders 166 each with an aperture on one end that house the LED and photodiode that minimizes ambient light and allows infra red light to pass between the photo emitter and detector, and does not require a separate optical viewing cuvette. The fault-tolerant alignment system assists in inserting the filtrate tube 124 into the blood leak detector and includes a retractable vane 170 that indicates the absence of the filtration tube by occluding the light path when the ultrafiltrate tube is not present. In addition, the transparent housing 162 prevents scratching of the optical surfaces of the bores, light source and light detector from multiple insertions of the ultrafiltrate tubing over the life of the detector by provision of recesses 169 in the tubing slot 163 that prevents the tubing from rubbing against the windows of the bores of the optical path. Since the photodiode and LED are housed within polymer cylinder housings 166 within transparent housing 162, the sensors and their electrical contacts are protected from liquid ingress.

The invention has been described in connection with what is presently considered to be the most practical and preferred embodiments. The invention is not to be limited to the disclosed embodiments, but, on the contrary, covers various modifications and equivalent arrangements included within the spirit and scope of the appended claims.

What is claimed is:

1. A blood leak detector comprising:
   a light source projecting a beam along an optical path, wherein the beam has a wavelength in a range of about 800 to 930 nm;
   a light detector receiving the beam through an aperture having a diameter in a range of 30 to 60 thousands of an inch;
   a housing having a slot to receive a tubular liquid passage between the light source and light detector, and where said slot is transverse to the optical path the slot has a width narrower than the tubular liquid passage when uncompressed, wherein the slot is exposed to ambient light which illuminates the tubular liquid passage while the blood leak detector is sensing for blood in the liquid passage, and
   a bore in the housing aligned with the optical path and with the light detector such that light from the light source passes through the bore before entering the detector, wherein the ambient light is blocked by the housing from shining directly to an end of the bore facing the detector.

2. The blood leak detector as in claim 1 wherein the light source projects through an aperture in a first sidewall in the leak detector and the light detector receives the beam through an aperture in a second sidewall, wherein the first and second sidewalls are on opposite sides of the slot.

3. The blood leak detector as in claim 2 wherein the apertures in the first and second sidewalls each have a diameter in a range of 30 to 60 thousands of an inch.

4. The blood leak detector as in claim 1 having wherein the slot has a width in a range of 50% to 90% of a width of the tubular liquid passage when uncompressed.

5. The blood leak detector as in claim 1 wherein the side walls each further comprise a recess aligned with the light source and light detector respectively, wherein said recess has an recessed wall that is not in contact with the tubular liquid passage and the recessed wall faces the tubular liquid passage.

6. The blood leak detector as in claim 5 wherein said recess in each of said side walls has a depth in a range of 0.010 to 0.060 inches.

7. The blood leak detector as in claim 1 wherein the light detector is responsive substantially only to the wavelength of the beam from the light source.

8. The blood leak detector as in claim 1 wherein the light source is cyclically turned on and off at a defined rate, and said light detector, during each cycle, senses a first light magnitude one when said source is on and a second light magnitude when said source is off.

9. The blood leak detector as in claim 1 wherein the slot is narrower than the liquid transport tube is squeezed when in the slot such that surfaces of the tube are flat against the a first transparent bore and the second transparent bore.

10. A blood leak detector comprising:
a housing having an upper surface with a slot to receive a liquid transport tube and a bottom surface with a cavity;
a module, fitted into the cavity of the housing body, further comprising a light source mounted in a first block of the module and a light detector mounted in a second block of the module, wherein a slot in the module between the first block and the second block aligns with the slot of the housing, and an optical path extends from said light source through the slots and to the light detector;
said first block includes a first transparent window aligned with the optical path and between the light source and the slot, and
said second block includes a second transparent window aligned with the optical path and between the light detector and the slot,
wherein the slot is exposed to ambient light that illuminates the liquid transport tube in the optical path and the slot, at the optical path, is narrower than the liquid transport tube in an uncompressed condition, and
a bore in ihe module aligned with the optical path and with the light detector such that light from the light source passes through the bore before entering the detector, wherein the ambient light does not shine directly to an end of the bore facing the detector.

11. The blood leak detector of claim 10 wherein said first block further comprises a first opaque casing for said light source, and said first opaque casing having a first transparent bore, and said second block further comprising a second opaque casing for said light detector and said second opaque casing having a second transparent bore, wherein the second transparent bore is the bore that does not allow ambient light to shine on the end of the bore.

12. The blood leak detector in claim 11 wherein the first and second opaque casings are each opaque cylinders having an end transparent plug forming the transparent bore.

13. The blood leak detector in claim 10 wherein the first block and second block each further comprise a side wall on opposite sides of the slot, and each of said side walls has a recess aligned with the optical path, wherein each recess is an open region in the corresponding side wall providing a gap between the liquid transport tube and the sidewall such that the liquid transport tube is not flush against a region of the side wall aligned with the optical path.

14. The blood leak detector in claim 13 wherein an inner surface of the recess is adjacent the window transparent to light emitted by said light source.

15. The blood leak detector in claim 14 wherein said windows are each in a respective one of the sidewalls is aligned with the optical path.

16. The blood leak detector in claim 10 wherein the housing body is substantially hemi-elliptical outer surface.

17. A method for detecting low blood concentrations in a liquid carrying tube using a blood leak detector having a light source, an optical path, a housing with a slot to receive the liquid carrying tube and a light sensor, said method comprising:

a. inserting the tube into the slot of the housing, wherein the slot is substantially narrower than the tube when uncompressed, such that the tube is pressed flat against side walls of the slot;
b. protecting optical surfaces of the light source and light sensor by recesses in the side walls separating said optical surfaces from the tube, wherein the optical surfaces are each a transparent aperture for each of the light source and light sensor;
c. projecting a light beam from the light source, through the aperture of the for the light source, the tube, the aperture for the light sensor and to the light sensor;
d. cyclically reading magnitudes of light received by the light sensor when the light source is projecting the beam and when the beam is not projected, and
e. determining an occurrence of a blood leak if a difference between the reading of the magnitude of light when the beam is projected and not projected falls below a threshold level.

18. A method to compensate for ambient light in an optical blood leak detector having a modulated light source, a light detector, a liquid path imposed between the light source and light detector, and a light detector circuit with a synchronous demodulator, said method comprising:
a. driving the light source to emit light at a certain modulation frequency along the liquid path and toward the light detector;
b. receiving the emitted light at the light detector and the light detector generating a signal indicative of the received light;
c. demodulating with the synchronous demodulator the signal generated by the light detector to isolate a portion of the signal corresponding to light detected at the certain modulation frequency; and
d. sensing extracorporeal blood in a liquid path external to a human body as the blood passes through the light path based on the isolated portion of the signal.

19. A blood leak detector comprising:
a light source projecting a beam along an optical path, wherein the beam has a wavelength in a range of about 800 to 930 nm;
a light detector receiving the beam;
a housing to receive a tubular liquid passage between the light source and light detector, said housing having a slot transverse to the optical path to receive the tubular liquid passage, wherein said slot adjacent the optical path has a width narrower than the tubular liquid passage when uncompressed, and
a bore in the housing aligned with the optical path and with the light detector such that light from the light source passes through the bore before entering the detector;
wherein the housing further comprises opposite side walls of the slot, and said side walls each having a recessed wall section comprising a window for the optical path, wherein a gap is between the window and the tubular liquid passage such that the window is not it contact with the tubular liquid passage when the passage, and
wherein the slot is exposed to ambient light which illuminates the liquid transport tube while the blood leak detector is sensing for blood in the liquid transport tube, and the housing blocks rays of the ambient light from shining directly into an inner end of the bore and the inner end of the bore facing the light detector.

20. A blood leak detector comprising:
a housing having an upper surface with a slot to receive a liquid transport tube, wherein the slot is exposed to ambient light which illuminates the liquid transport tube while the blood leak detector is sensing for blood in the liquid transport tube;
a first opaque housing in the housing body and adjacent a side of the slot;
a light source in the first opaque housing;
a light detector in a second opaque housing in the housing body and adjacent an opposite side of the slot, wherein an optical path extends from said light source through the slot and to the light detector;
said first opaque casing further comprises a first transparent bore aligned with the optical path and between the light source and the slot, and
said second opaque casing further comprises a second transparent bore aligned with the optical path and between the light detector and the slot;
wherein the housing blocks rays of the ambient light from shining directly to an inner end of the second transparent bore and the inner end of the bore faces the light detector.

21. The blood leak detector in claim 20 wherein the first and second opaque casings are each opaque cylinders having an end aperture with a transparent plug forming the transparent bore.

22. The blood leak detector in claim 20 wherein the first and second transparent bores include a cylindrical plug transparent to light from the light source.

23. The blood leak detector as in claim 20 wherein the slot is narrower than the liquid transport tube is squeezed when in the slot such that surfaces of the tube are flat against the a first transparent bore and the second transparent bore.

24. A blood leak detector comprising:
a housing body having an upper surface with a slot to receive a liquid transport tube and a bottom surface with a cavity;
a module fitted into the cavity of the housing body, and said module further comprising a light source mounted in a first block of the module and a light detector mounted in a second block of the module, wherein a slot between the first block and the second block aligns with the slot of the housing body, and an optical path extends from said light source through the slot and to the light detector, wherein the slot is exposed to ambient light that illuminates the liquid transport tube while the blood leak detector is sensing for blood in the liquid transport tube;
said first block includes a first transparent bore aligned with the optical path and between the light source and the slot;
said second block includes a second transparent bore aligned with the optical path and between the light detector and the slot, and
wherein the first block and second block each further comprise a side wall of the slot, and each of said side walls has a recess for the first and second transparent bores respectively, wherein each recess is an open region in the corresponding side wall having a first end flush with the side wall and a second end aligned with an end of one of the transparent bores, and
wherein the slot is narrower at the optical path than the liquid transport tube when the tube is uncompressed, and the side wall prevents ambient light shining directly to an end of the second transparent bore facing the light detector.

25. The blood leak detector in claim 24 wherein the second end of the recess is adjacent a window portion of the side wall transparent to light emitted by said light source.

26. The blood leak detector in claim 24 wherein said window portion of the side wall is aligned with the optical path.

27. A blood leak detector comprising:
a housing having a slot to receive a transparent tubing;
a light source projecting a beam along an optical path through an aperture, wherein the beam has a wavelength in a range of about 800 to 930 nm;
a light detector receiving the beam through an aperture, and
a retractable vane aligned with the slot and having an extended position extending into the slot to block the beam upstream of the light detector and a retracted position unblocking the beam, wherein said vane is biased to the extended position and is displaced to the retracted position by tubing inserted in the slot.

28. The blood leak detector in claim 27 wherein the light detector is responsive substantially only to the wavelength of the beam from the light source.

29. The blood leak detector in claim 27 wherein the light beam is cyclically turned on and off at a defined rate, and, during each cycle, said light detector generates a first signal when the light beam is on and a second signal when the light source is off.

30. The blood leak detector in claim 27 wherein the vane further comprises a spring biasing said vane in the extended position.

31. The blood leak detector in claim 27 wherein the vane is biased towards the extended position by gravity.

32. The blood leak detector in claim 27 wherein the vane is moved to a retracted position by a filtrate tube inserted in the detector.

33. The blood leak detector in claim 27 wherein the vane is opaque to the light beam.

34. A blood leak detector comprising:
a housing having a slot to receive a transparent tubing;
a light source projecting a beam along an optical path,
a light detector receiving the beam, and
a retractable vane aligned with the slot and having an extended position extending into the slot to block the beam upstream of the light detector and a retracted position unblocking the beam, wherein said vane is biased to the extended position and is displaced to the retracted position by tubing inserted in the slot.

35. The blood leak detector in claim 34 wherein the light detector is responsive substantially only to the wavelength of the beam from the light source.

36. The blood leak detector in claim 34 wherein the light beam is cyclically turned on and off at a defined rate, and, during each cycle, said light detector generates a first signal when the light beam is on and a second signal when the light source is off.

37. The blood leak detector in claim 34 wherein the vane further comprises a spring biasing said vane in the extended position.

38. The blood leak detector as in claim 34 wherein the vane is biased towards the extended position by gravity.

39. The blood leak detector in claim 34 wherein the vane is moved to a retracted position by a filtrate tube inserted in the detector.

40. The blood leak detector as in claim 34 wherein the vane is opaque to the light beam.

* * * * *